(12) United States Patent
Day et al.

(10) Patent No.: US 11,052,193 B2
(45) Date of Patent: Jul. 6, 2021

(54) SYSTEM FOR MONITORING AND DELIVERING MEDICATION TO A PATIENT AND METHOD OF USING THE SAME TO MINIMIZE THE RISKS ASSOCIATED WITH AUTOMATED THERAPY

(71) Applicant: ICU Medical, Inc., San Clemente, CA (US)

(72) Inventors: William Kenneth Day, Hoffman Estates, IL (US); Timothy L. Ruchti, Gurnee, IL (US)

(73) Assignee: ICU Medical Inc., San Clemente, CA (US)

( * ) Notice: Subject to any disclaimer, the term of this patent is extended or adjusted under 35 U.S.C. 154(b) by 0 days.

(21) Appl. No.: 16/865,087

(22) Filed: May 1, 2020

(65) Prior Publication Data

US 2020/0330685 A1    Oct. 22, 2020

Related U.S. Application Data

(63) Continuation of application No. 16/435,206, filed on Jun. 7, 2019, now Pat. No. 10,646,651, which is a (Continued)

(51) Int. Cl.
*A61M 5/172*     (2006.01)
*G16H 20/17*     (2018.01)
(Continued)

(52) U.S. Cl.
CPC .......... *A61M 5/1723* (2013.01); *G16H 20/10* (2018.01); *G16H 20/17* (2018.01); *A61M 5/365* (2013.01);
(Continued)

(58) Field of Classification Search
CPC . A61B 5/00; A61M 1/00; A61M 5/00; A61M 5/142; A61M 5/166; A61M 5/172;
(Continued)

(56) References Cited

U.S. PATENT DOCUMENTS 6,039,251 A    3/2000  Holowko et al.
6,892,278 B2   5/2005  Ebergen
(Continued)

FOREIGN PATENT DOCUMENTS

JP    2007-525256    9/2007
JP    2011-506048    3/2011
(Continued)

OTHER PUBLICATIONS

"Context-Free Grammar", Wikipedia.org, as last modified Mar. 5, 2010 in 11 pages, https://en.wikipedia.org/w/index.php/?title=Context-free_grammar&oldid=347915989.
(Continued)

*Primary Examiner* — Eric Blount
(74) *Attorney, Agent, or Firm* — Knobbe Martens Olson & Bear, LLP (57) ABSTRACT

A system and method for monitoring and delivering medication to a patient. The system includes a controller that has a control algorithm and a closed loop control that monitors the control algorithm. A sensor is in communication with the controller and monitors a medical condition. A rule based application in the controller receives data from the sensor and the closed loop control and compares the data to predetermined medical information to determine the risk of automation of therapy to the patient. A system monitor is also in communication with the controller to monitor system, remote system, and network activity and conditions. The controller then provides a predetermined risk threshold where below the predetermined risk threshold automated
(Continued)

closed loop medication therapy is provided. If the predetermined risk threshold is met or exceeded, automated therapy adjustments may not occur and user/clinician intervention is requested.

18 Claims, 5 Drawing Sheets

Related U.S. Application Data continuation of application No. 15/664,785, filed on Jul. 31, 2017, now Pat. No. 10,314,974, which is a continuation of application No. 14/739,840, filed on Jun. 15, 2015, now Pat. No. 9,724,470.

(60) Provisional application No. 62/012,756, filed on Jun. 16, 2014.

(51) Int. Cl.
  *G16H 20/10* (2018.01)
  *A61M 5/36* (2006.01)
  *A61M 5/168* (2006.01)
  *A61M 5/142* (2006.01)

(52) U.S. Cl.
  CPC ............ *A61M 2005/14208* (2013.01); *A61M 2005/16863* (2013.01); *A61M 2205/16* (2013.01); *A61M 2205/18* (2013.01); *A61M 2205/3553* (2013.01)

(58) Field of Classification Search
  CPC .... A61M 31/00; A61M 5/1723; A61M 5/365; A61M 2005/14208; A61M 2005/16863; A61M 2205/16; A61M 2205/18; A61M 2205/3553; G06F 19/00
  USPC .......................................... 340/540; 604/506
  See application file for complete search history.

(56) References Cited

U.S. PATENT DOCUMENTS

| | | | |
|---|---|---|---|
| 7,398,279 B2 | 7/2008 | Muno, Jr. et al. | |
| 7,976,508 B2 | 7/2011 | Hoag | |
| 8,075,514 B2 | 12/2011 | Butterfield et al. | |
| 8,398,592 B2 | 3/2013 | Leibner-Druska | |
| 8,626,530 B1 | 1/2014 | Tran et al. | |
| 9,886,550 B2 | 2/2018 | Lee et al. | |
| 9,943,269 B2 | 4/2018 | Muhsin et al. | |
| 10,430,761 B2 | 10/2019 | Hume et al. | |
| 10,434,246 B2 | 10/2019 | Silkaitis et al. | |
| 10,463,788 B2 | 11/2019 | Day | |
| 10,617,815 B2 | 4/2020 | Day et al. | |
| 10,646,651 B2 | 5/2020 | Day et al. | |
| 10,692,595 B2 | 6/2020 | Xavier et al. | |
| 10,741,280 B2 | 8/2020 | Xavier et al. | |
| 10,765,799 B2 | 9/2020 | Belkin et al. | |
| 10,799,632 B2 | 10/2020 | Kohlbrecher | |
| 10,812,380 B2 | 10/2020 | Jha et al. | |
| 2002/0013551 A1 | 1/2002 | Zaitsu et al. | |
| 2002/0077852 A1* | 6/2002 | Ford | G16H 40/40 705/2 |
| 2002/0173702 A1 | 11/2002 | Lebel et al. | |
| 2002/0173875 A1 | 11/2002 | Wallace et al. | |
| 2003/0036744 A1 | 2/2003 | Struys et al. | |
| 2003/0212821 A1 | 11/2003 | Gillies et al. | |
| 2004/0139004 A1 | 7/2004 | Cohen et al. | |
| 2005/0102167 A1 | 5/2005 | Kapoor | |
| 2005/0240305 A1* | 10/2005 | Bogash | G16H 20/13 700/242 |
| 2005/0261660 A1 | 11/2005 | Choi | |
| 2005/0273367 A1 | 12/2005 | Nourie et al. | |
| 2006/0129140 A1 | 6/2006 | Todd et al. | |
| 2006/0173927 A1 | 8/2006 | Beyer et al. | |
| 2007/0061393 A1 | 3/2007 | Moore | |
| 2007/0213684 A1 | 9/2007 | Hickle et al. | |
| 2007/0233035 A1* | 10/2007 | Wehba | A61M 5/142 604/500 |
| 2008/0033966 A1 | 2/2008 | Wahl | |
| 2008/0259926 A1 | 10/2008 | Tavares et al. | |
| 2009/0150878 A1 | 6/2009 | Pathak et al. | |
| 2009/0177146 A1* | 7/2009 | Nesbitt | A61M 5/14 604/66 |
| 2009/0292340 A1 | 11/2009 | Mass et al. | |
| 2010/0036310 A1* | 2/2010 | Hillman | A61M 5/142 604/20 |
| 2010/0056992 A1* | 3/2010 | Hayter | A61B 5/14532 604/66 |
| 2010/0121752 A1 | 5/2010 | Banigan et al. | |
| 2010/0174266 A1 | 7/2010 | Estes | |
| 2010/0274218 A1 | 10/2010 | Yodfat et al. | |
| 2010/0298765 A1* | 11/2010 | Budiman | A61B 5/4839 604/66 |
| 2010/0318025 A1* | 12/2010 | John | A61M 5/1408 604/84 |
| 2011/0021898 A1 | 1/2011 | Wei et al. | |
| 2011/0138185 A1 | 6/2011 | Ju et al. | |
| 2011/0196748 A1 | 8/2011 | Caron et al. | |
| 2012/0005680 A1 | 1/2012 | Dolby et al. | |
| 2012/0036102 A1 | 2/2012 | Fletcher et al. | |
| 2012/0157920 A1 | 6/2012 | Flachbart et al. | |
| 2012/0283630 A1 | 11/2012 | Lee et al. | |
| 2013/0012877 A1 | 1/2013 | Debelser et al. | |
| 2013/0150824 A1 | 6/2013 | Estes et al. | |
| 2013/0158504 A1* | 6/2013 | Ruchti | G16H 40/67 604/504 |
| 2013/0317753 A1 | 11/2013 | Kamen et al. | |
| 2013/0346108 A1 | 12/2013 | Kamen et al. | |
| 2014/0025392 A1 | 1/2014 | Chandrasenan | |
| 2014/0180711 A1 | 6/2014 | Kamen et al. | |
| 2014/0276571 A1 | 9/2014 | Ludolph | |
| 2014/0288947 A1 | 9/2014 | Simpson et al. | |
| 2014/0297329 A1 | 10/2014 | Rock | |
| 2015/0161354 A1 | 6/2015 | Blomquist | |
| 2015/0199192 A1 | 7/2015 | Borges et al. | |
| 2015/0230760 A1 | 8/2015 | Schneider | |
| 2015/0328396 A1 | 11/2015 | Adams et al. | |
| 2015/0371004 A1 | 12/2015 | Jones | |
| 2016/0034655 A1 | 2/2016 | Gray et al. | |
| 2016/0045661 A1 | 2/2016 | Gray et al. | |
| 2016/0241391 A1 | 8/2016 | Fenster | |
| 2017/0262590 A1 | 9/2017 | Karakosta et al. | |
| 2018/0121613 A1 | 5/2018 | Connely, IV et al. | |
| 2018/0181712 A1 | 6/2018 | Ensey et al. | |
| 2018/0247712 A1 | 8/2018 | Muhsin et al. | |
| 2019/0006044 A1 | 1/2019 | Brask | |
| 2019/0132196 A1 | 5/2019 | Trivedi et al. | |
| 2019/0228863 A1 | 7/2019 | Dharwad et al. | |
| 2019/0240405 A1 | 8/2019 | Wehba et al. | |
| 2019/0243829 A1 | 8/2019 | Butler et al. | |
| 2019/0311803 A1 | 10/2019 | Kohlbrecher et al. | |
| 2019/0392929 A1 | 12/2019 | Gassman | |
| 2020/0027541 A1 | 1/2020 | Xavier et al. | |
| 2020/0027542 A1 | 1/2020 | Xavier et al. | |
| 2020/0027543 A1 | 1/2020 | Xavier et al. | |
| 2020/0027548 A1 | 1/2020 | Xavier et al. | |
| 2020/0027549 A1 | 1/2020 | Xavier et al. | |
| 2020/0027550 A1 | 1/2020 | Xavier et al. | |
| 2020/0027551 A1 | 1/2020 | Xavier et al. | |
| 2020/0028837 A1 | 1/2020 | Xavier et al. | |
| 2020/0028914 A1 | 1/2020 | Xavier et al. | |
| 2020/0035355 A1 | 1/2020 | Xavier et al. | |
| 2020/0061291 A1 | 2/2020 | Day et al. | |
| 2020/0206413 A1 | 7/2020 | Silkaitis et al. | |
| 2020/0306443 A1 | 10/2020 | Day | |
| 2020/0335194 A1 | 10/2020 | Jacobson et al. | |

(56) References Cited

U.S. PATENT DOCUMENTS

FOREIGN PATENT DOCUMENTS

| | | |
|---|---|---|
| JP | 2012-011204 | 1/2012 |
| JP | 2012-523895 | 10/2012 |
| JP | 2014-068283 | 4/2014 |
| WO | WO 2019/219290 | 11/2019 |

OTHER PUBLICATIONS

"Download", Free On-Line Dictionary of Computing, as archived Jun. 16, 2010 in 1 page, http://web.archive.org/web/20100616010314/https://foldoc.org/download.

Edworthy, Judy, "Medical Audible Alarms: A Review", Journal of the American Medical Informatics Association, vol. 20, No. 3, 2013, pp. 584-589.

International Search Report and Written Opinion received in PCT Application No. PCT/US2015/036058, dated Sep. 16, 2015 in 8 pages.

"Software Versioning", Wikipedia.org, dated Oct. 16, 2011 in 11 pages, https://en.wikipedia.org/w/index.php?title=Software_versioning&oldid=455859110.

\* cited by examiner

SYSTEM FOR MONITORING AND DELIVERING MEDICATION TO A PATIENT AND METHOD OF USING THE SAME TO MINIMIZE THE RISKS ASSOCIATED WITH AUTOMATED THERAPY

CROSS-REFERENCE TO RELATED APPLICATIONS

This application is a continuation of U.S. patent application Ser. No. 16/435,206, entitled "System for Monitoring and Delivering Medication to a Patient and Method of Using the Same to Minimize the Risks Associated with Automated Therapy," filed Jun. 7, 2019, which is a continuation of U.S. patent application Ser. No. 15/664,785, entitled "System for Monitoring and Delivering Medication to a Patient and Method of Using the Same to Minimize the Risks Associated with Automated Therapy," filed Jul. 31, 2017, now U.S. Pat. No. 10,314,974, which is a continuation of U.S. patent application Ser. No. 14/739,840, entitled "System for Monitoring and Delivering Medication to a Patient and Method of Using the Same to Minimize the Risks Associated with Automated Therapy," filed Jun. 15, 2015, now U.S. Pat. No. 9,724,470, which claims the benefit of priority to U.S. Provisional Patent Application No. 62/012,756, entitled "System for Monitoring and Delivering Medication to a Patient and Method of Using the Same to Minimize the Risks Associated with Automated Therapy," filed Jun. 16, 2014, the disclosures of which are hereby incorporated by reference in their entirety.

BACKGROUND OF THE INVENTION

This invention relates to a system for monitoring and delivering medication to a patient. More specifically, the present invention is directed toward a device that monitors the risk to a patient of an automated therapy decision and allows a clinician to customize rules that determine whether an automated change in therapy is to be allowed or whether user/clinician intervention should be required based upon the risk of automation and the customized rules.

Diabetes is a metabolic disorder that afflicts tens of millions of people throughout the world. Diabetes results from the inability of the body to properly utilize and metabolize carbohydrates, particularly glucose. Normally, the finely tuned balance between glucose in the blood and glucose in bodily tissue cells is maintained by insulin, a hormone produced by the pancreas which controls, among other things, the transfer of glucose from blood into body tissue cells. Upsetting this balance causes many complications and pathologies including heart disease, coronary and peripheral artery sclerosis, peripheral neuropathies, retinal damage, cataracts, hypertension, coma, and death from hypoglycemic shock.

In patients with insulin-dependent diabetes the symptoms of the disease can be controlled by administering additional insulin (or other agents that have similar effects) by injection or by external or implantable insulin pumps. The correct insulin dosage is a function of the level of glucose in the blood. Ideally, insulin administration should be continuously readjusted in response to changes in blood glucose level. In diabetes management, insulin enables the uptake of glucose by the body's cells from the blood. Glucagon acts opposite to insulin and causes the liver to release glucose into the blood stream. The basal rate is the rate of continuous supply of insulin provided by an insulin delivery device (pump). The bolus is the specific amount of insulin that is given to raise blood concentration of the insulin to an effective level when needed (as opposed to continuous).

Presently, systems are available for continuously monitoring blood glucose levels by inserting a glucose sensitive probe into the patient's subcutaneous layer or vascular compartment or, alternately, by periodically drawing blood from a vascular access point to a sensor. Such probes measure various properties of blood or other tissues including optical absorption, electrochemical potential, and enzymatic products. The output of such sensors can be communicated to a hand held device that is used to calculate an appropriate dosage of insulin to be delivered into the blood stream in view of several factors such as a patient's present glucose level and rate of change, insulin administration rate, carbohydrates consumed or to be consumed, steroid usage, renal and hepatic status and exercise. These calculations can then be used to control a pump that delivers the insulin either at a controlled basal rate or as a periodic or onetime bolus. When provided as an integrated system the continuous glucose monitor, controller, and pump work together to provide continuous glucose monitoring and insulin pump control.

Such systems at present require intervention by a patient or clinician to calculate and control the amount of insulin to be delivered. However, there may be periods when the patient is not able to adjust insulin delivery. For example, when the patient is sleeping he or she cannot intervene in the delivery of insulin yet control of a patient's glucose level is still necessary. A system capable of integrating and automating the functions of glucose monitoring and controlled insulin delivery would be useful in assisting patients in maintaining their glucose levels, especially during periods of the day when they are unable to intervene.

Alternately, in the hospital environment an optimal glucose management system involves frequent adjustments to insulin delivery rates in response to the variables previously mentioned. However, constant intervention on the part of the clinician is burdensome and most glucose management systems are designed to maximize the time interval between insulin updates. A system capable of safely automating low-risk decisions for insulin delivery would be useful in improving patient insulin therapy and supporting clinician workflow.

Since the year 2000 at least five continuous or semi-continuous glucose monitors have received regulatory approval. In combination with continuous subcutaneous insulin infusion (CSII), these devices have promoted research toward closed loop systems which deliver insulin according to real time needs as opposed to open loop systems which lack the real time responsiveness to changing glucose levels. A closed loop system, also called the artificial pancreas, consists of three components: a glucose monitoring device such as a continuous glucose monitor (CGM) that measures subcutaneous glucose concentration (SC); a titrating algorithm to compute the amount of analyte such as insulin and/or glucagon to be delivered; and one or more analyte pumps to deliver computed analyte doses subcutaneously. Several prototype systems have been developed, tested, and reported based on evaluation in clinical and simulated home settings. This concerted effort promises accelerated progress toward home testing of closed loop systems.

Similarly, closed loop systems have been proposed for the hospital setting and investigational devices have been developed and tested, primarily through animal studies. In addition, several manufacturers are either in the process of developing or have submitted to the FDA automated glucose measurement systems designed for inpatient testing. Such systems will accelerate the development of fully automated systems for inpatient glucose management.

The primary problem with closed loop control or full automation of insulin therapy is that a computerized system makes decisions that may be high risk in terms of potential consequences if the patient's condition changes or differs from the assumptions behind the computerized decision system. As a result of the automation these high risk decisions are not uncovered until the risk is realized and the patient displays an unacceptable medical condition. Second, in the event of a device failure or medication management system or MMS failure, action is required by the automated system despite the potential lack of information. Third, in scenarios in which frequent glucose measurements are automatically collected but automation is not desired, it is undesirable to update the infusion at the same frequency as glucose measurements are collected. Fourth, when user intervention is required it may be undesirable or difficult for a clinician to respond at the bedside. For example, if the patient is in an isolation room but is observable the clinician may desire to update the infusion rate without entering the room.

Thus, a principle object of the invention is to provide an improved system for monitoring and delivering medication to a patient that makes risk determinations before providing therapy.

Another object of the invention is to provide a system that minimizes patient risk by mapping device failure, patient state and condition, and uncertainty.

Yet another object of the invention is to provide a system for monitoring and delivering medication to a patient that minimizes the risk to a patient.

Another object of the invention is to provide a system for monitoring and delivering medication that is able to selectively request for a user intervention.

These and other objects, features, or advantages of the invention will become apparent from the specification and claims.

SUMMARY OF THE INVENTION

A system for monitoring and delivering medication to a patient and the method of using the same. The system has a controller that has an adjustment or control algorithm and an automation risk monitor that monitors the control algorithm. More specifically, the present invention is directed toward a system and method that monitors the risk to a patient of an automated therapy decision and allows a clinician to customize rules that determine whether an automated change in therapy is to be allowed or whether user/clinician intervention should be required based upon the risk of automation and the customized rules. Thus, the risk of potential adverse consequences to the patient if the patient's condition changes or differs from the assumptions behind the computerized or automated decision system can be minimized.

A sensor in communication with the controller monitors a medical condition to provide data to a rule based application in the controller. In addition, the rule based application receives data from the closed loop control and compares the data to predetermined medical information to determine the risk to the patient. When the risk is below a predetermined risk threshold, medication or therapy adjustments are allowed to occur in an automated manner according to a closed loop algorithm. Alternatively, when the risk is above the predetermined risk threshold, the controller triggers a request for user intervention or reduces the degree of automated therapy allowed.

A system monitor in communication with the controller monitors conditions and activity of the system and remote system. Upon detection of a system failure the system monitor provides data to the controller to determine whether to adjust treatment, message a clinician, and send an alarm. Similarly, the system monitor tracks network activity to detect network failures or failures of remote systems such as a clinician messaging system. Depending on the conditions presented an alarm system escalates the alarm sent.

DETAILED DESCRIPTION OF THE PREFERRED EMBODIMENT

Figure 1:
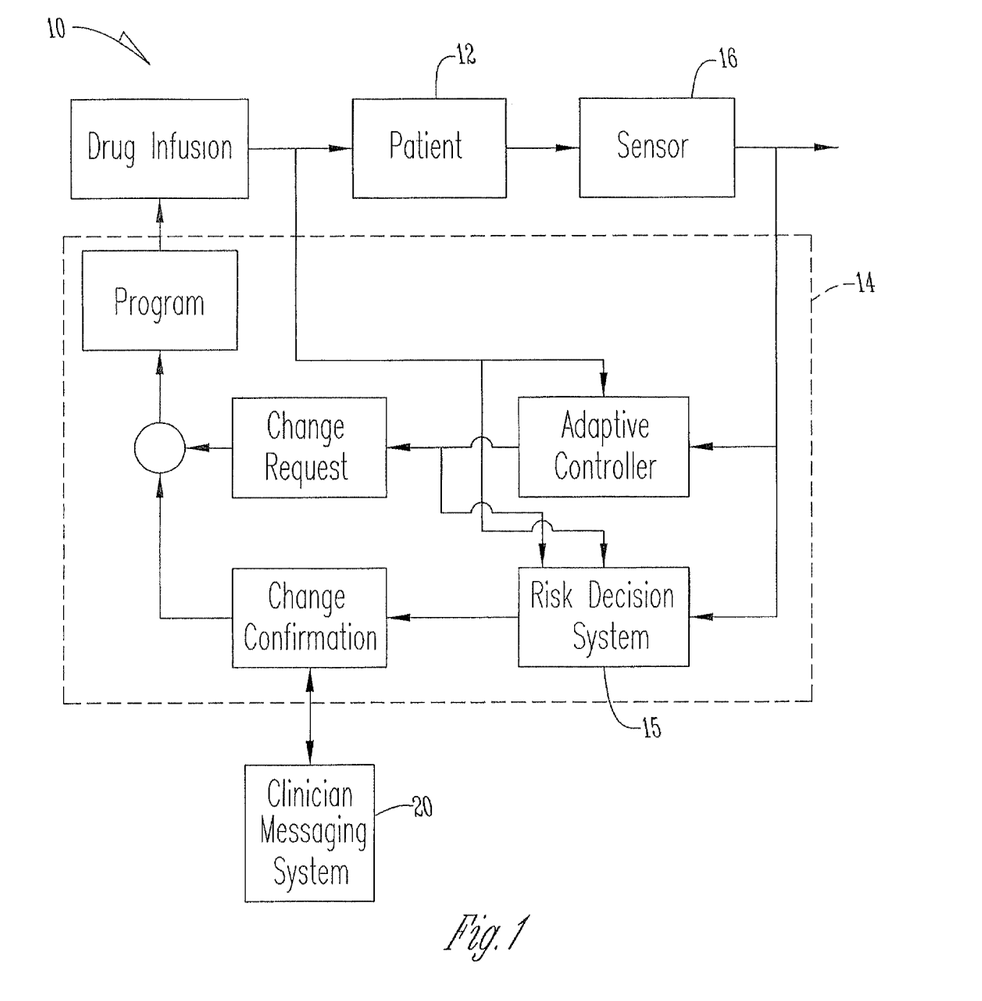
FIG. 1 is a schematic diagram of a closed loop control system augmented with the automation risk monitor of the invention.
Figure 4:
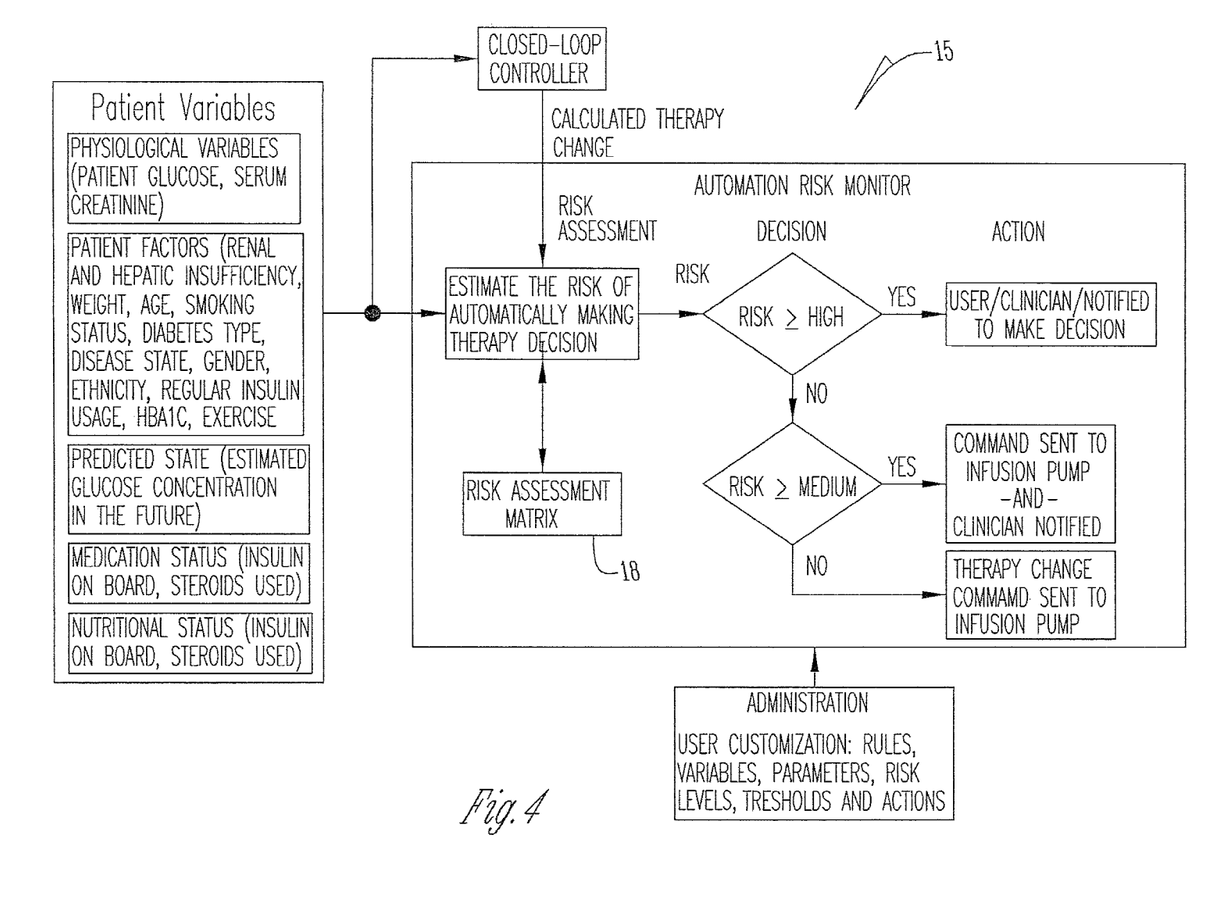
FIG. 4 is a schematic diagram of an automation risk monitor system.

FIG. 1 provides a system 10 for monitoring and delivering medication, such as insulin, to a patient 12. The system 10 includes a controller 14 that utilizes a control algorithm and an automation risk monitor 15 all presented in a closed loop. A sensor 16 is in communication with the controller 14 and monitors a medical condition of the patient 12. A rule based application 18 (see FIG. 4 for example) in the automation risk monitor of the controller 14 receives data from the sensor 16 and compares the data to predetermined medical information to determine the risk to the patient 12 to automate the delivery of medication.

The rule based application 18 can be set to assess the therapy being administered and its criticality. Further, the rule based application 18 can assess currently administered drugs and 15 patient 12 characteristics such as food intake, fluid intake, and disease state. Patient physiological response variables such as vitals, labs, and cognitive assessments can also be set to be used by the rule based application 18 to determine the risk to the patient. The rule based application 18 can also be set to include factors related to patient risk parameters such as change in patient state and transitions in therapy such as beginning, continuing, changing, or ending therapy.

The rule based application 18 in one embodiment includes physician or clinician entered conditions of when automation is acceptable. Clinician entered conditions can include therapy importance such as critical, life sustaining, supplementary, and benign. Further, the clinician can establish fail-safe, fail-operate, and fail-stop conditions for infusion that are based on strict rules or based on ranges of conditions. The system 10 is thus in communication with a clinician messaging system 20 that communicates to a clinician when the risk of automation is unacceptable. In a preferred embodiment the messaging system is remote from the system 10.

The rule based application 18 in one embodiment can include a risk profile wherein a clinician implements a risk profile according to a metric that may be qualitative (low, medium or 30 high) or quantitative (1-10 where 10 is the highest risk) and a threshold defining when intervention is required. In either case, a quantitative metric is internally calculated and compared to a quantitative threshold. For example, in the case of low, medium or high each qualitative measurement is assigned a quantitative value such as 2, 5 and 7 respectively. Consequently, a risk scale is specified and a threshold above which intervention is requested. The rule based application 18 can also include a risk matrix that is developed to enable a determination of risk. Although the matrix is ultimately stored internally, it can be parameterized by the user. One example of the risk matrix is shown below:

| Glucose Range (mg/dL) | Glucose Δ (derivative) | Calculated Δ in Insulin | Risk Level |
|---|---|---|---|
| 0-70 | Increasing | Increasing | High |
| 0-70 | Increasing | Decreasing | Low |
| 0-70 | Decreasing | Increasing | High |
| 0-70 | Decreasing | Decreasing | Low |
| 70-90 | Increasing | Increasing | Medium |
| 70-90 | Increasing | Decreasing | Low |
| 70-90 | Decreasing | Increasing | High |
| 70-90 | Decreasing | Decreasing | Low |
| 90-120 | Increasing | Increasing | Medium |
| 90-120 | Increasing | Decreasing | Low |
| 90-120 | Decreasing | Increasing | High |
| 90-120 | Decreasing | Decreasing | Low |
| 120-180 | Increasing | Increasing | Low |
| 120-180 | Increasing | Decreasing | Low |
| 120-180 | Decreasing | Increasing | Medium |
| 120-180 | Decreasing | Decreasing | Low |
| 180-250 | Increasing | Increasing | Low |
| 180-250 | Increasing | Decreasing | High |
| 180-250 | Decreasing | Increasing | Medium |
| 180-250 | Decreasing | Decreasing | Low |
| Above 250 | Increasing | Increasing | High |
| Above 250 | Increasing | Decreasing | Low |
| Above 250 | Decreasing | Increasing | Low |
| Above 250 | Decreasing | Decreasing | Medium |

Specifically, the second column is the calculated or requested insulin level from the closed loop controller. The table is an example of how the treatment condition is mapped to a risk level. There are numerous other methods for implementing this information which may include continuous mapping functions, fuzzy logic, probability calculations and the like.

A second way to provide this type of system is to employ an insulin/glucose pharmacokinetic/pharmacodynamic model as shown below which predicts the future glucose level. The clinician can then use a predicted value rather than or in addition to glucose level and a derivative.

$$\dot{G}(t) = -p_G \cdot G(t) - S_I(t) \cdot G \cdot \frac{Q(t)}{1 + \alpha_G Q(t)} + \frac{P(t) + EGP - CNS}{V_G} \quad (1)$$

$$\dot{I}(t) = -n\frac{I(t)}{1 + \alpha_I I(t)} + \frac{u_{ex}(t)}{V_I} + \frac{u_{en}(t)}{V_I}$$

$$\dot{P}_1(t) = -d_1 P_1(t) + P_e(t)$$

$$\dot{P}_2(t) = -\min(d_2 P_2(t), P_{max}) + d_1 P_1(t)$$

$$P(t) = \min(d_2 P_2(t), P_{max}) + P_N(t)$$

$$\dot{G}(t) = -p_G(t)G(t) - S_I(t)G(t)\frac{Q(t)}{1 + \alpha_G Q(t)} + \frac{P(t)}{V_G}$$

$$\dot{Q}(t) = -kQ(t) + KI(t) \quad (2)$$

$$\dot{I}(t) = -n\frac{I(t)}{1 + \alpha_I I(t)} = \frac{u_{ex}(t)}{V_I} \quad (3)$$

In Equations (1)-(3), G(t) [mmol/L] denotes the total plasma glucose concentration, and I(t) [mU/L] is the plasma insulin concentration. The effect of previously infused insulin being utilized over time is represented by Q(t) [mU/L], with k [l/min] accounting for the effective life of insulin in the system. Exogenous insulin infusion rate is represented by $u_{ex}(t)$ [mU/min], whereas P(t) [mmol/L min] is the exogenous glucose infusion rate. Patient's endogenous glucose removal and insulin sensitivity through time are described by $p_G(t)$ [l/min] and $S_I(t)$ [L/mU min], respectively. The parameters $V_I$ [L] and $V_G$ [L] stand for insulin and glucose distribution volumes. n [l/min] is the first order decay rate of insulin from plasma. Two Michaelis-Menten constants are used to describe saturation, with $\alpha_I$ [L/mU] used for the saturation of plasma insulin disappearance, and $\alpha_G$ [L/mU] for the saturation of insulin-dependent glucose clearance.

Thus, the rule based application 18 determines the risk to a patient 12 by determining a predetermined risk threshold. Below the predetermined risk threshold, because low risk is detected, the system 10 can move forward in an automated fashion and provide medication as required. If the risk is determined to be above the predetermined risk threshold the controller triggers a request for user intervention by contacting the clinician messaging system 20 instead of moving forward with automation.

The system 10 can also be used to monitor any form of infusion including anticoagulation monitoring during heparin infusion, respiratory monitoring during pain medication infusion such as morphine, and hemodynamic monitoring during infusion of vaso-active medication for cardio vascular support.

As best understood in view of FIGS. 1-5, in an alternative embodiment the system 10 includes a system monitor 22 that is in communication with the controller 14. In one arrangement the system monitor 22 tracks network activity on a network 30 to determine whether a network failure has occurred. The system 22 also detects interruptions in communication with decision support provided by a remote system 23. Similarly, the system monitor 22 tracks network activity to determine whether an interruption has occurred between the system 10 and the clinician messaging system 20 or other remote system 23 that allows for remote operation of the system 10 by a clinician or other basis of support such as medical record tracking. In the event that an interruption is detected the system 10 is enabled to continue infusion at either a backup infusion rate set by a clinician or the rule based application 18. Alternatively, the system 10 can be configured to set an infusion rate based on a default setting that can include a minimum or maximum rate that depends on the physiological state of the patient 12 and the therapy being administered.

Figure 5:
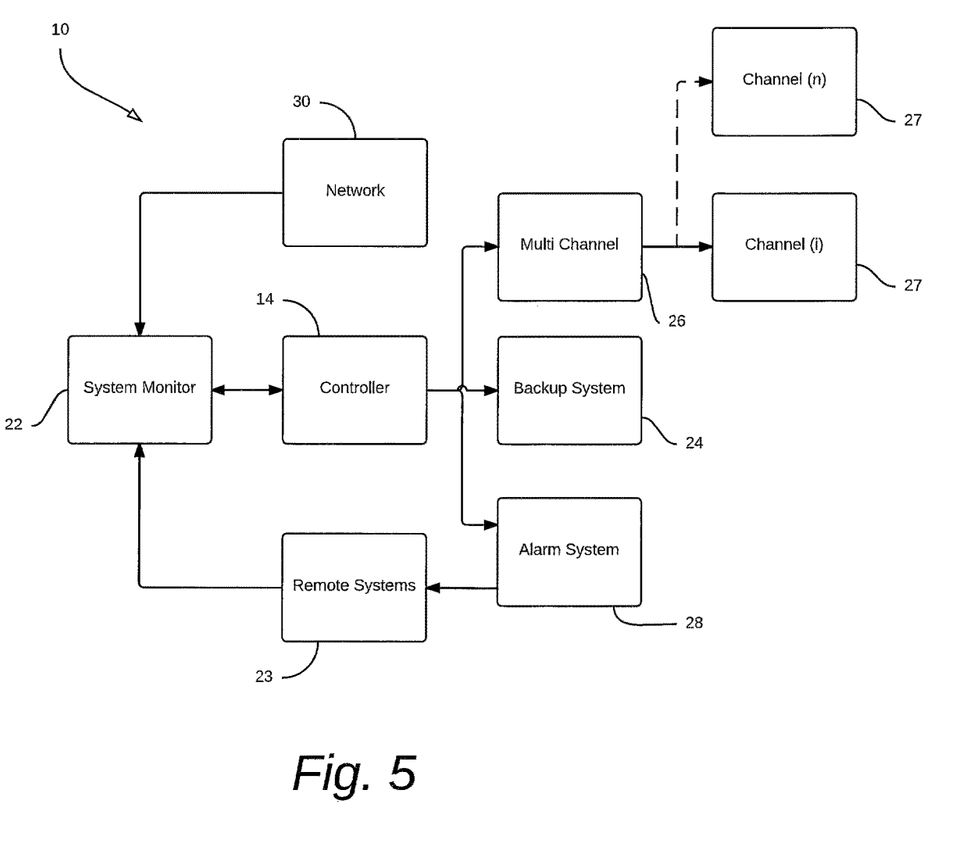
FIG. 5 is a schematic diagram of a closed loop control system augmented with the system monitor of the invention.

In another embodiment the system monitor 22 detects air in line levels. In this embodiment the system monitor 22 determines whether the amount of air present in line is at a critical level that requires stopping the infusion. When air in line is detected the system monitor 22 sends data to the controller 14 that uses the automation risk monitor 15 to determine whether the criticality of treatment is sufficient to allow the system 10 to continue to operate. In one arrangement, when air is detected by the system monitor 22 an alarm is sent via the clinician messaging system 20 or emitted from the system 10 locally. The system monitor 22 also determines whether the detection of air in line is a false positive and if a false positive is detected the alarm is auto-cleared. The system monitor 22 can also be set to not send an alarm if the amount of air present is non-critical.

Additionally, the system monitor 22 detects whether an occlusion is present. If an occlusion is detected the system monitor 22 sends data to the controller 14 to determine whether the occlusion poses a sufficient risk to adjust the infusion rate. Alternatively, if the controller 14 determines a sufficient risk is presented by an occlusion an alarm can be triggered or a message can be sent via the clinician messaging system 20. In one arrangement the presence of occlusions is based on occlusion pressure levels.

In the event that the system monitor 22 detects a sufficient amount of air or large enough occlusion the system 10 can activate a backup system 24. For example, in a life-sustaining situation, a backup system 24 would be enabled and the infusion rate set by the controller 14. In one arrangement, the backup system 24 maintains infusion parameters set by the system 10 so that treatment can be transitioned without interruption.

In another arrangement the system 10 includes a multichannel infusion system 26 that allows for multiple treatment paths or channels 27. When the system monitor 22 detects that one channel 27 has failed the system 10 switches to an alternative channel 27 to deliver the infusion. In one embodiment the system 10 adjusts the infusion rate of a concurrently infused medication to compensate for the failure of a channel 27. For example, if a dextrose infusion fails in a hypoglycemic patient 12 the system 10 can increase the infusion of nutrition to compensate for the lack of dextrose being infused.

In one embodiment, the system monitor 22 tracks whether input is received from clinicians after the clinician is contacted via the clinician monitoring system 20 to input or confirm a therapy adjustment. If the clinician fails to respond the system monitor 22 sends data to the controller 14 to adjust treatment based on information from the automation risk monitor 15 as described previously.

An alarm system 28 can also be included in the system 10. The alarm system 28 determines the appropriate alarm to send depending on the level of patient risk, uncertainty, and predicted outcomes. In this manner, the alarm system 28 provides the highest degree of alarm in association with critical events that require immediate attention.

Figure 2:
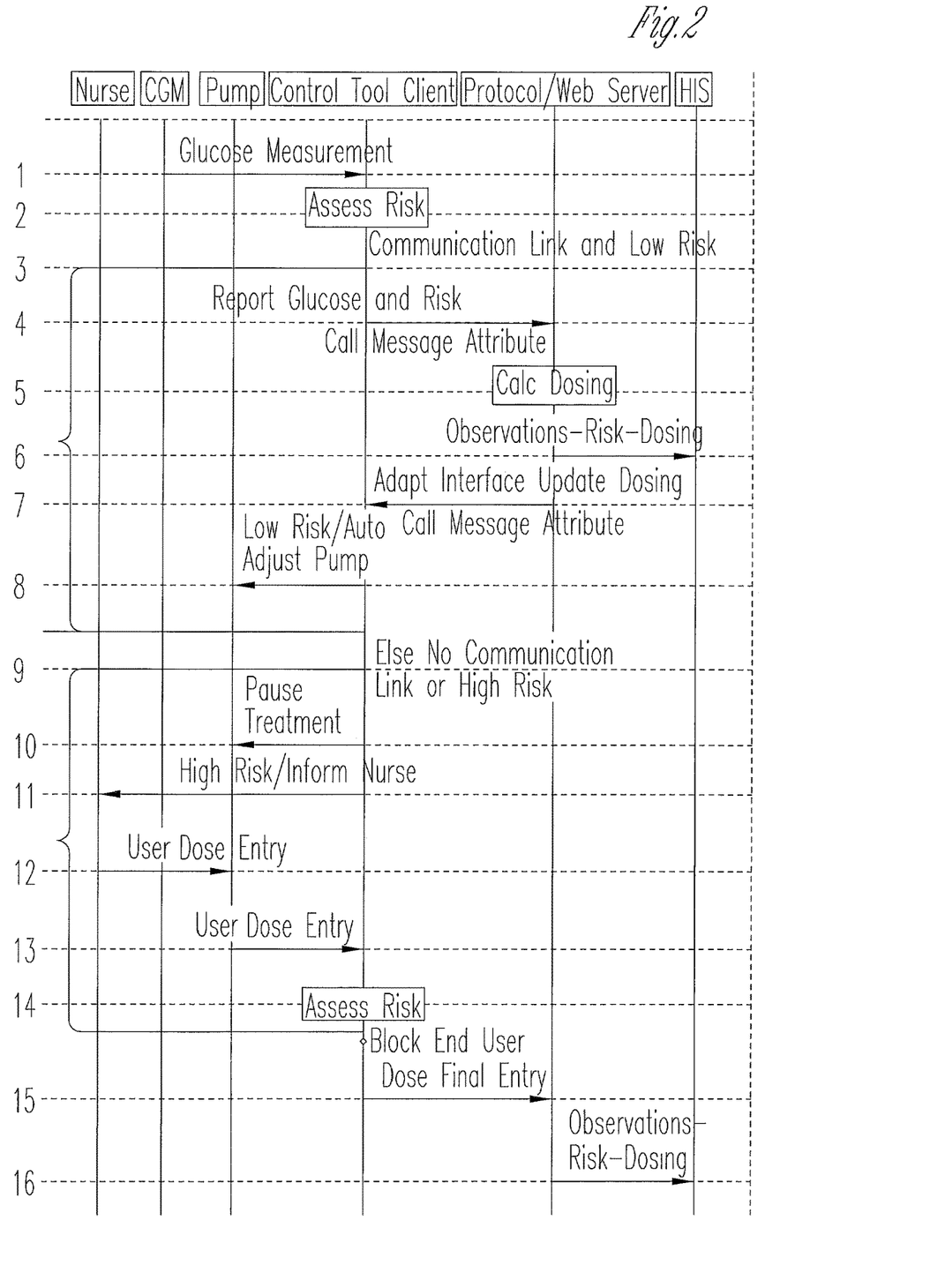
FIG. 2 is an example messaging diagram for the invention.

In operation, the system 10 monitors a control algorithm of a controller 14 to receive data. The controller 14 additionally receives continuous data from a sensor 16 regarding a medical condition such as a glucose level. The controller 14 then compares the data from the control algorithm and the sensor 16 to predetermined medical information so that the controller 14 can determine a predetermined risk threshold of automating the delivery of medication. Then, based on the data, if a risk is below a predetermined threshold, automation is permitted and a command or request for medication or insulin is provided to the insulin pump. Therefore the insulin delivery rate is automatically updated according to the algorithm model or closed loop controller used. Alternatively, if the risk is at or above a predetermined threshold a request for user intervention is triggered sending a message to the clinician messaging system 20 so that a user may intervene to make a determination regarding whether the medication should be provided. The request for intervention is generated and sent directly to the user through a messaging system that is bi-directional. The message system 20 provides information and requests a user response. When the response is related to a change in therapy an authentication step is included.

The response to a request is provided by the user directly through the user interface of the system. Alternatively, the response can be returned through an authenticated messaging system involving a unique identifier specific to a positive or negative response. In the event that the clinician fails to respond the therapy may be continued at a lower rate or stopped altogether. Optionally, an alarm can be generated by the alarm system 28.

Figure 3:
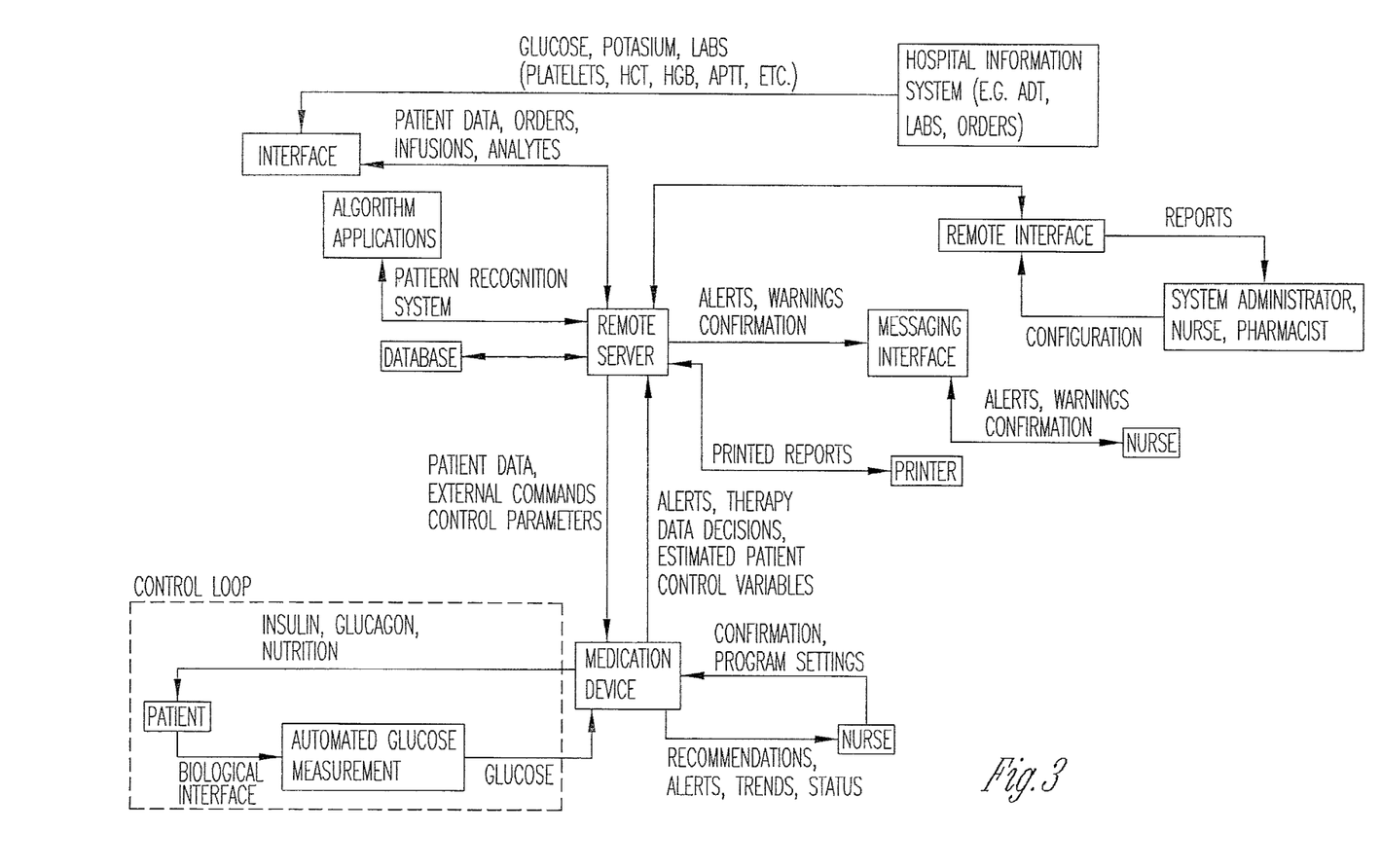
FIG. 3 is a schematic diagram showing the architecture of a semi automatic glucose management system.

During the course of normal operation glucose measurements may be received that generate a change in the recommended insulin. However, the change may not be significant enough to provide a therapeutic advantage to the patient versus the burden of requesting confirmation from the nurse. Consequently, a rule based application 18 is provided which evaluates therapy changes to trigger a request for an automatic update or nursing intervention. The input to the rule based application 18 includes the blood glucose level, the change in glucose, the insulin infusion, the recommended change in insulin infusion, the estimated insulin on board, and the predicted glucose in the future. Rules involving comparisons to thresholds, regression equations, and calculations are created which trigger a therapy update based on the inputs.

In the event that an interruption to the normal operation of the system 10, the remote systems 23, or network 30 is detected by the system monitor 22, the system adjusts therapy by altering the infusion rate of the system 10 or switching to a backup system 24. Additionally, if an interruption is detected in a system 10 using multi-channel infusions 26, the system 10 can alter the infusion rate or channel 27 used for infusing to compensate for the channel 27 failure.

When a command request is made or an interruption to normal operation is detected an alarm system 28 determines the appropriate alarm to send. The highest alarm is sent by the alarm system 28 based on the most critical failures of the system 10 or risks to the patient 12.

Thus, the present system can be used to make determinations of treatment decisions requiring user intervention based upon a diagnostic value, the change in diagnostic value, the current drug infusion rate, the updated drug infusion rate, the treatment target range, network failures, system failures, and clinician inactivity. In addition, the system notifies a clinician that intervention is required and receives the implementing clinician instruction in response to the notification.

An additional advantage is presented because the system 10 determines when clinician intervention is necessary and unnecessary. Specifically, system 10 is independent of an adaptive control algorithm or a computerized protocol. The system 10 functions as a supervisor that watches the performance of the closed loop system. Consequently, data from the closed loop system and diagnostic sensor 16 are provided to the rule based application 18 that uses a matrix to produce a quantitative level of risk. The level of risk can be expressed as a discrete general level such as the "High", "Low" and "Medium" values expressed in the table above or the level of risk can be a numerical value, score, index or percentage. The risk is compared to a particular risk threshold to either generate and/or provide an "okay" to proceed with therapy or to trigger a request for user intervention.

This operation differs from current systems that do not determine risk of automation. Instead prior art systems allow automation to occur regardless of potential risk and then when sensors indicate a patient is experiencing an unacceptable medical condition a clinician is alerted. Therefore the system 10 provides an advantage of preventing the unacceptable medical condition from occurring in the first place as a result of monitoring the automation process and predetermining risks of automation.

A further advantage is found in that the system 10 detects failures of the system 10, remote systems 23, networks 30, and inactivity of clinicians. Upon detection of one of these failures or risks posed to a patient the alarm system 28 escalates alarms based on the risk or risks posed to the patient 12 based on changes to the patient 12 or the system 10. Thus, at the very least all of the stated objectives have been met.

What is claimed is:

1. A system for operating an infusion system, the system comprising one or more hardware processors configured to:
   control a pump that is configured to deliver a drug to a patient according to a first infusion rate;
   detect failure in an infusion system or a remote system that is in network communication with the infusion system;
   stop the delivery of the drug according to the first infusion rate based on the detected failure;
   assess a first risk of stopping further delivery of the drug versus a second risk corresponding to the detected failure; and
   determine whether to continue delivery of the drug according a second infusion rate that is different than the first infusion rate based on the assessment of the first risk with the second risk.

2. The system of claim 1, wherein the drug is insulin.

3. The system of claim 1, wherein the failure comprises a network failure.

4. The system of claim 1, wherein the failure comprises air in an infusion line.

5. The system of claim 1, wherein the failure comprises occlusion of an infusion line.

6. The system of claim 1, wherein the one or more hardware processors are configured to deliver the drug at a predetermined rate after the detected failure.

7. The system of claim 1, wherein the one or more hardware processors are configured to notify a clinician system based on the detected failure.

8. The system of claim 1, wherein the estimation of first risk is determined on a supervisory computing system that is independent from the infusion system.

9. The system of claim 1, wherein the one or more hardware processors are configured to completely stop delivery of the drug based on the assessment indicating that the first risk of stopping is lower than the second risk corresponding to the detected failure.

10. A method for operating an infusion system, the method comprising:
    controlling a pump that is configured to deliver a drug to a patient according to a first infusion rate;
    detecting failure in an infusion system or a remote system that is in network communication with the infusion system;
    stop the delivery of the drug according to the first infusion rate based on the detected failure;
    assessing a first risk of stopping further delivery of the drug versus a second risk corresponding to the detected failure; and
    determining whether to continue delivery of the drug according to a second infusion rate that is different than the first infusion rate based on the assessment of the first risk with the second risk.

11. The method of claim 10, wherein the drug is insulin.

12. The method of claim 10, wherein the failure comprises a network failure.

13. The method of claim 10, wherein the failure comprises air in an infusion line.

14. The method of claim 10, wherein the failure comprises occlusion of an infusion line.

15. The method of claim 10, further comprising delivering the drug at a predetermined rate after the detected failure.

16. The method of claim 10, further comprising notifying a clinician system based on the detected failure.

17. The method of claim 10, wherein the estimation of first risk is determined on a supervisory computing system that is independent from the infusion system.

18. The method of claim 10, further comprising completely stopping delivery of the drug based on the assessment indicating that the first risk of stopping is lower than the second risk corresponding to the detected failure.

* * * * *